(12) United States Patent
Alniami

(10) Patent No.: US 11,457,803 B1
(45) Date of Patent: Oct. 4, 2022

(54) LUNG SCOPE ASSEMBLY

(71) Applicant: Laith Ismail Alniami, Palmdale, CA (US)

(72) Inventor: Laith Ismail Alniami, Palmdale, CA (US)

( * ) Notice: Subject to any disclaimer, the term of this patent is extended or adjusted under 35 U.S.C. 154(b) by 0 days.

(21) Appl. No.: 17/824,710

(22) Filed: May 25, 2022

(51) Int. Cl.
| | |
|---|---|
| *A61B 34/20* | (2016.01) |
| *A61B 1/267* | (2006.01) |
| *H04N 7/18* | (2006.01) |
| *H04N 5/247* | (2006.01) |
| *A61B 1/00* | (2006.01) |
| *A61B 1/015* | (2006.01) |
| *A61B 1/06* | (2006.01) |
| *H04N 5/225* | (2006.01) |

(52) U.S. Cl.
CPC ........ *A61B 1/2676* (2013.01); *A61B 1/00016* (2013.01); *A61B 1/00082* (2013.01); *A61B 1/00087* (2013.01); *A61B 1/015* (2013.01); *A61B 1/0684* (2013.01); *H04N 5/247* (2013.01); *H04N 7/181* (2013.01); *H04N 2005/2255* (2013.01)

(58) Field of Classification Search
CPC .............. A61B 1/2676; A61B 1/00016; A61B 1/00082; A61B 1/00087; A61B 1/015; A61B 1/0684; H04N 5/247; H04N 7/181; H04N 2005/2255
See application file for complete search history.

(56) References Cited

U.S. PATENT DOCUMENTS

| | | | |
|---|---|---|---|
| 2018/0036084 A1* | 2/2018 | Krimsky | A61B 34/10 |
| 2019/0142262 A1* | 5/2019 | Inglis | A61B 1/00048 600/188 |
| 2020/0221927 A1* | 7/2020 | Matthison-Hansen | A61B 1/015 |
| 2021/0137350 A1* | 5/2021 | Inglis | A61B 1/0051 |

* cited by examiner

*Primary Examiner* — Howard D Brown, Jr.
(74) *Attorney, Agent, or Firm* — Plager Schack LLP; Mark H. Plager; Michael J. O'Brien

(57) ABSTRACT

A lung endoscopy system is configured to provide portable data to a health care provider. The lung endoscopy system has a handle housing, attached to a primary screen, a second screen, a third screen, and a fourth screen. An inflatable ball is joined to the housing and electrically coupled to a ball valve inflate switch, a ball valve deflate switch, and a pump. A power connection is electrically coupled to a power connector and an external power source on a wheel cart. A camera switch is electrically coupled to a left middle camera, a right middle camera, a 180-degree camera, and a front entry camera arranged on the handle housing. The left middle camera, the right middle camera, the 180-degree camera, and the front entry camera are electrically coupled to at least one monitor on the wheel cart, and a second screen with a camera extension line.

6 Claims, 5 Drawing Sheets

LUNG SCOPE ASSEMBLY

BACKGROUND

The embodiments herein relate generally to medical devices.

Prior to embodiments of the disclosed invention, it was difficult to conduct a lung scope in a remote area. Embodiments of the disclosed invention solve this problem.

SUMMARY

A lung endoscopy system is configured to provide portable data to a health care provider. The lung endoscopy system has a handle housing, attached to a primary screen, a second screen, a third screen, and a fourth screen. An inflatable ball is joined to the housing and electrically coupled to a ball valve inflate switch, a ball valve deflate switch, and a pump. A power connection is electrically coupled to a power connector and an external power source on a wheel cart. A camera switch is electrically coupled to a left middle camera, a right middle camera, a 180-degree camera, and a front entry camera arranged on the handle housing. The left middle camera, the right middle camera, the 180-degree camera, and the front entry camera are electrically coupled to at least one monitor on the wheel cart, and a second screen with a camera extension line.

In some embodiments, a Wi-Fi television connection can be communicatively coupled to the handle housing and configured to transmit to visual data to an external television screen. A burn switch can be arranged on the handle housing, joined to a knife with a burn line attached to the wheel cart. A vacuum switch can be arranged on the handle housing, and joined coupled to the wheel cart with a vacuum line at a vacuum source. A freeze switch can be arranged on the handle housing, and joined to the wheel cart with a freeze line. A camera light switch can be arranged on the handle housing and electrically coupled to a first LED on the left middle camera, a second LED on the right middle camera, a third LED on the 180-degree camera, and a fourth LED on the front entry camera.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
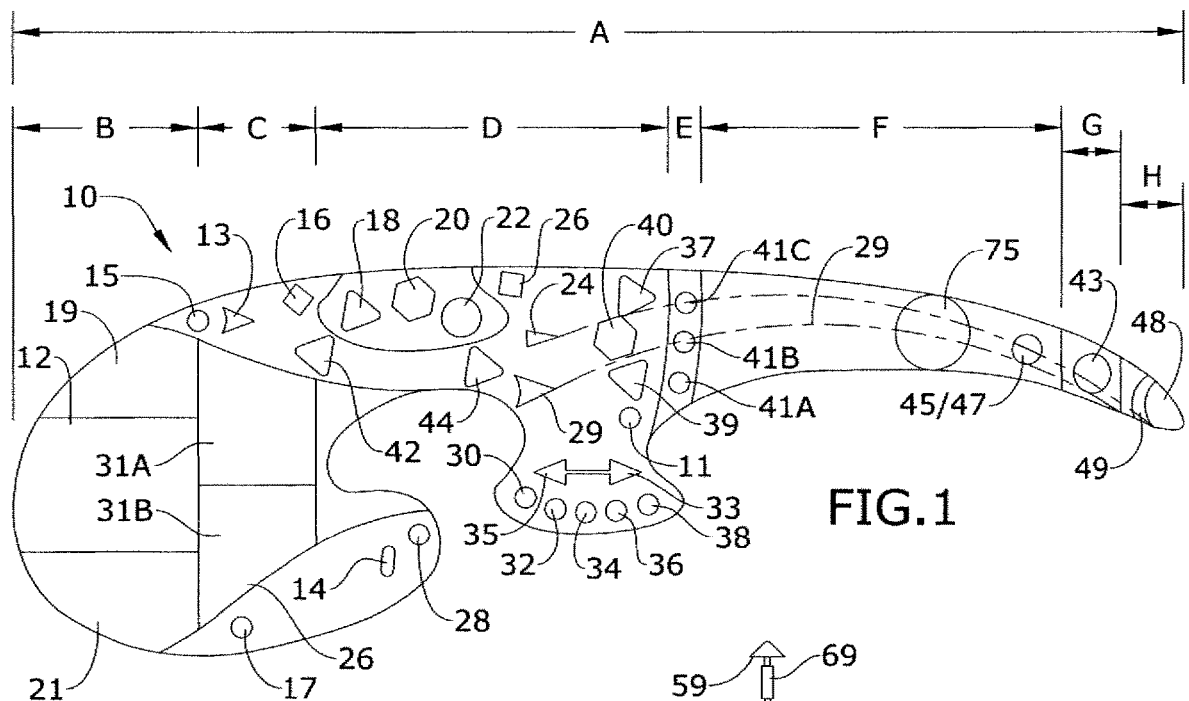
FIG. 1 shows a schematic view of one embodiment of the present invention.
Figure 2:
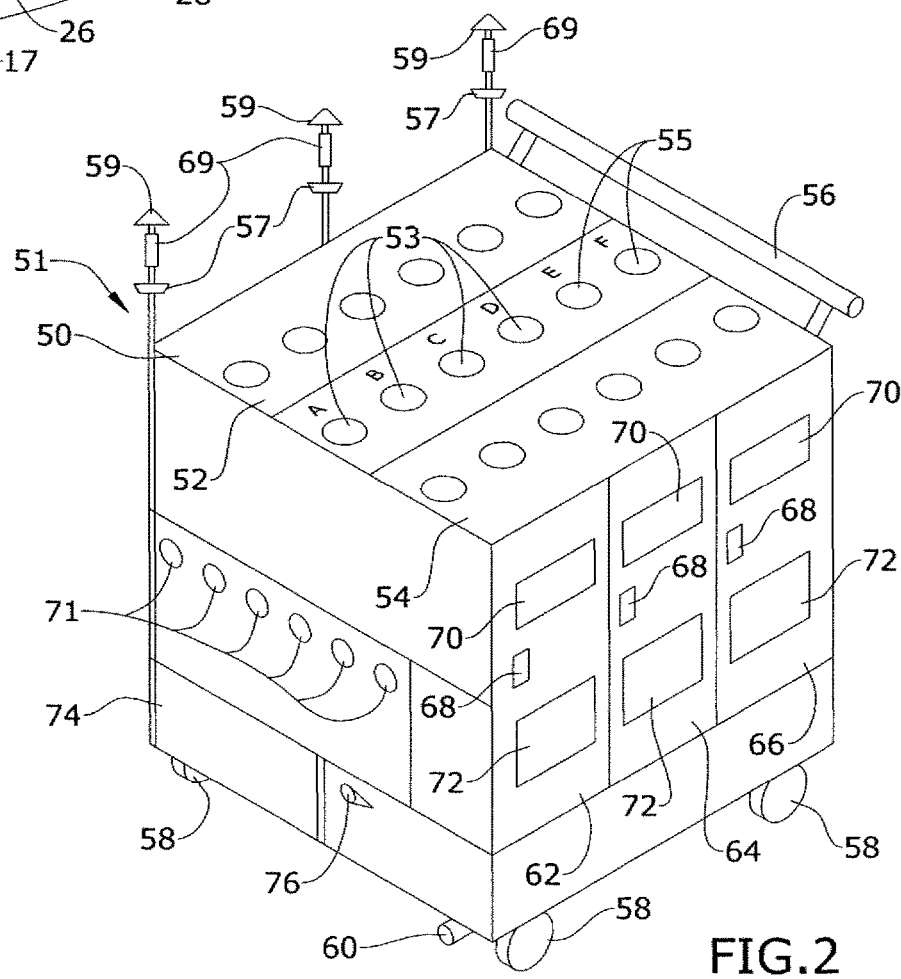
FIG. 2 shows a schematic view of one embodiment of the present invention.
Figure 3:
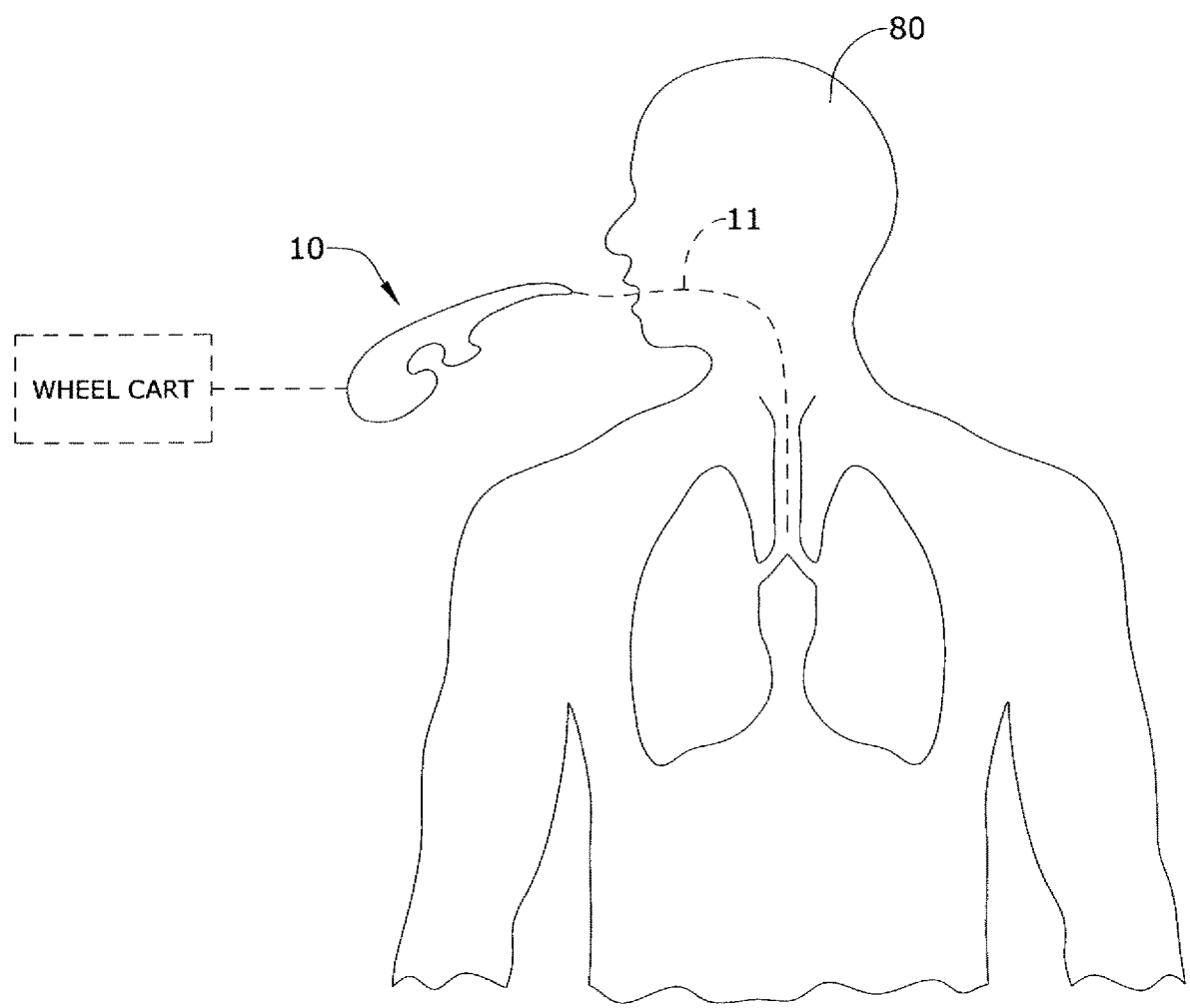
FIG. 3 shows a schematic view of one embodiment of the present invention shown in use.
Figure 4:
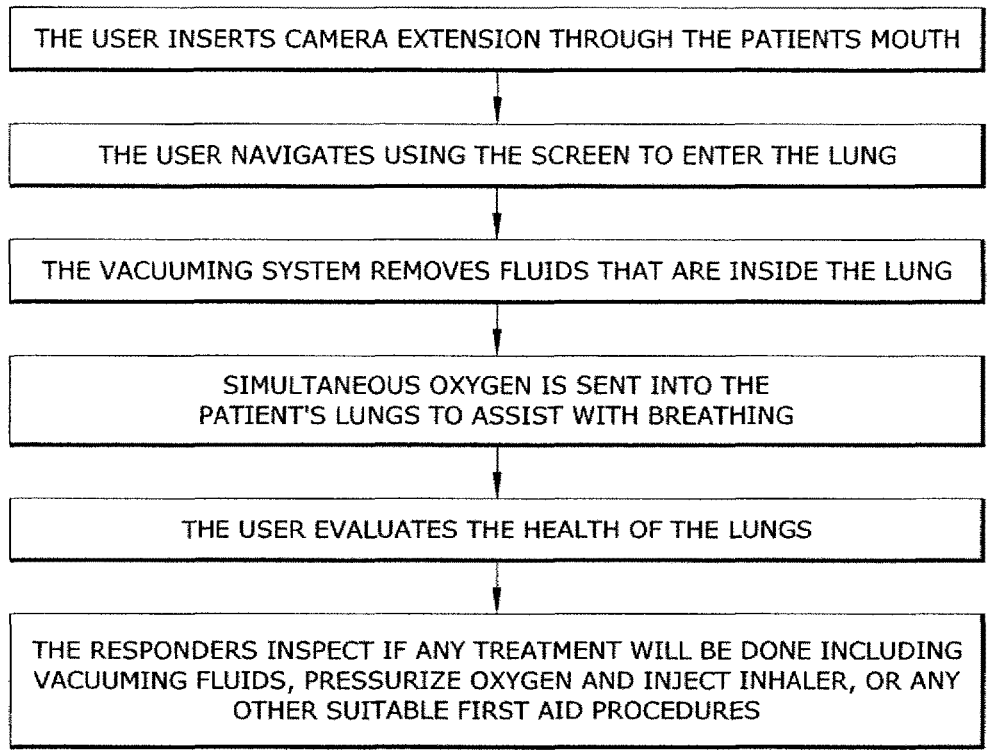
FIG. 4 shows a flow chart of one embodiment of the present invention.

By way of example, and referring to FIG. 1 and FIG. 2, one embodiment of a lung endoscopy system 10 is configured to provide portable data to a health care provider. The lung endoscopy system 10 comprises a housing, attached to a primary screen 12, a second screen 31A, a third screen 31B, and a fourth screen 70. An inflatable ball 43 is joined to the housing and electrically coupled to a ball valve switch 13, a ball valve deflate switch 15, and a pump.

A Wi-Fi television connection 14 is configured to transmit to visual data to an external television screen. A burn switch 14 is electrically coupled to a knife with a burn line 36. A power connection 17 is electrically coupled to a power connector 28 and an external power source on a wheel cart 50. A vacuum switch 18 is electrically coupled to the wheel cart 50 with a vacuum line 32 at a vacuum source 71. A left middle camera 19 and a right middle camera 21 are attached to the housing.

The freeze switch 20 is attached to the wheel cart 50 with a freeze line 38. An oxygen switch 22 is attached to the wheel cart 50 with an oxygen line 30. An inhaler 24 is arranged through the housing and can be used to distribute inhaled medicine to a patient. A camera switch and light 26 is electrically coupled to the left middle camera 19, the right middle camera 21, a 180-degree camera 45, a front entry camera 48, and an injection line with needle 29. The left middle camera 19, the right middle camera 21, the 180-degree camera 45, and the front entry camera 48 are electrically coupled to at least one monitor 70 on the wheel cart 50, the second screen 31A, the third screen 31B with a camera extension line 11.

A camera light switch 13 is electrically coupled to a first LED on the left middle camera 19, a second LED on the right middle camera 21, a third LED on the 180-degree camera 45, and a fourth LED on the front entry camera 48 connected to the primary screen 12.

The wheel cart 50 further comprises a housing configured which is attached to three posts 51. The three posts 51 have a hanger 57, an LED 59, and a vibrator 69. The vibrator 69 can be useful for accessing swollen tissue. The housing is attached a handle 56, and a plurality of wheels 58. The housing can accommodate fluid containers 52 and oxygen cylinders 54. Cavities 53 can be used to accommodate an adult sized lung endoscopy device 10. Cavities 55 can be used to accommodate a child sized lung endoscopy device 10. The monitors 70 are mounted on the housing. A maintenance cover 72 permits a user to access internal components of the wheel cart 50. A waste water tank 74 is arranged in the wheel cart 50. A mouth guard 75 is arranged on the lung endoscopy system 10. The mouth guard can be made in six different sizes, depending on the size of the patient's mouth. A clean water supply 76 is attached to the tank.

To use the device, a user first inserts the lung endoscopy system in the patient's mouth 90. Then the extension passes through the patient's mouth 80 into the patient's lungs. The user navigates using the screen 70 to enter the lung. The vacuuming system removes fluids that are inside the lung. Simultaneously oxygen is sent into the patient's lungs to assist with breathing. the user evaluates the health of the lungs with data from the 360-degree camera 48. the responders inspect if any treatment will be done including vacuuming fluids, pressurize oxygen and inject inhaler, or any other suitable first aid procedures.

Figure 5:
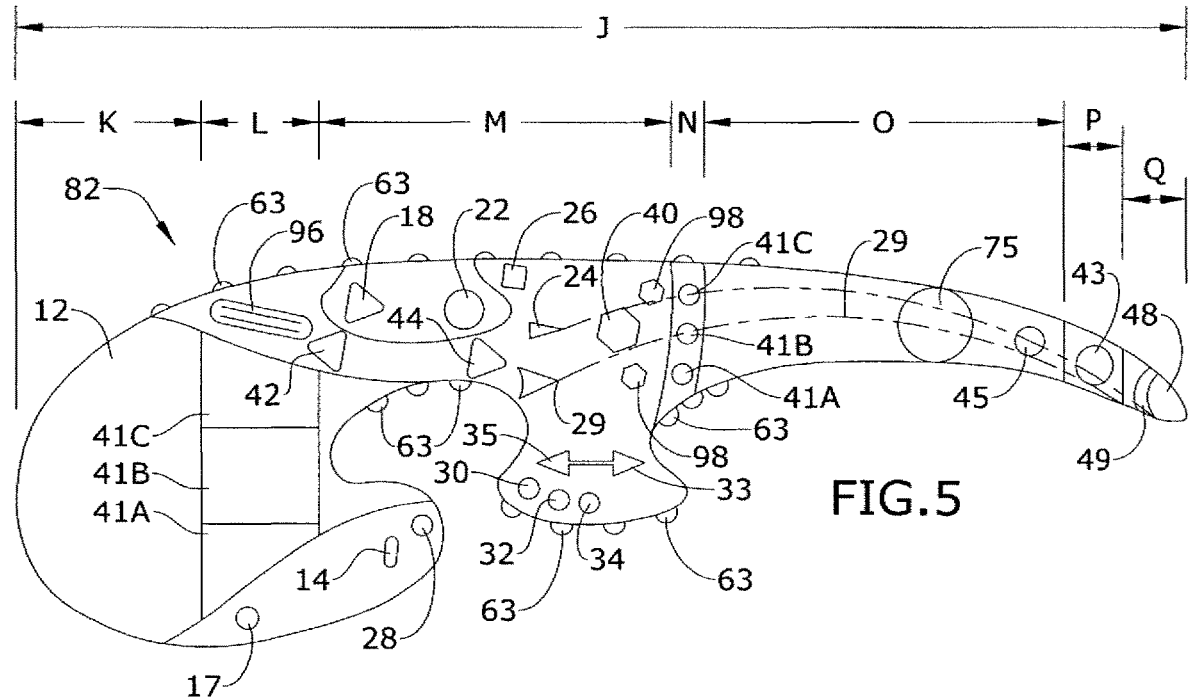
FIG. 5 shows a schematic view of one embodiment of the present invention.

Turning to FIG. 5, a first responder lung endoscopy device 12 comprises: an air pressure reader 96 is attached to the housing. A plurality of 180-degree cameras 45 and 47 provide visual data to be displayed on the screen by the user.

Figure 6:
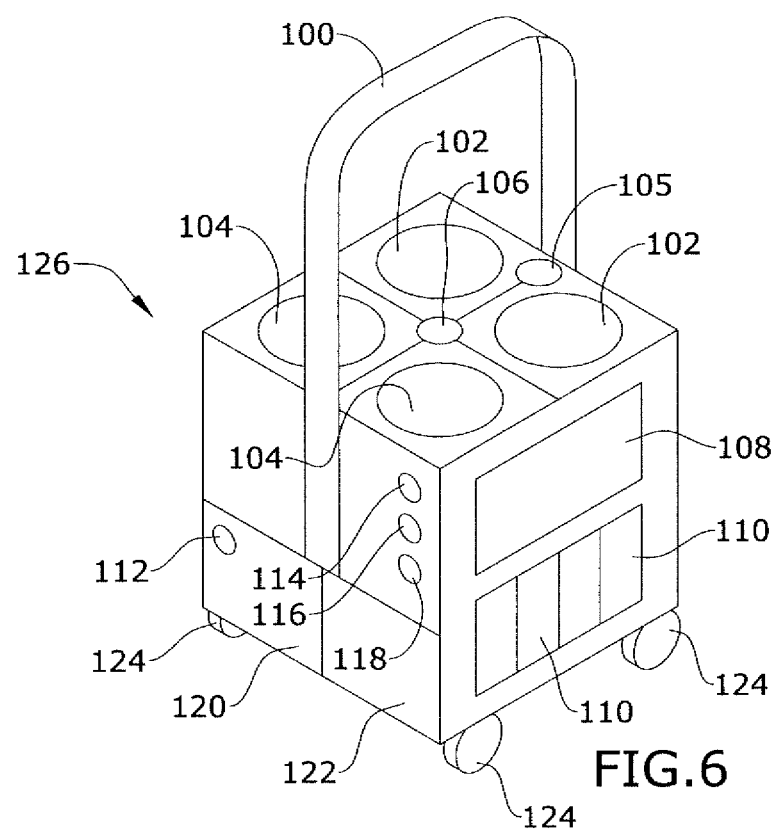
FIG. 6 shows a schematic view of one embodiment of the present invention.
Figure 7:
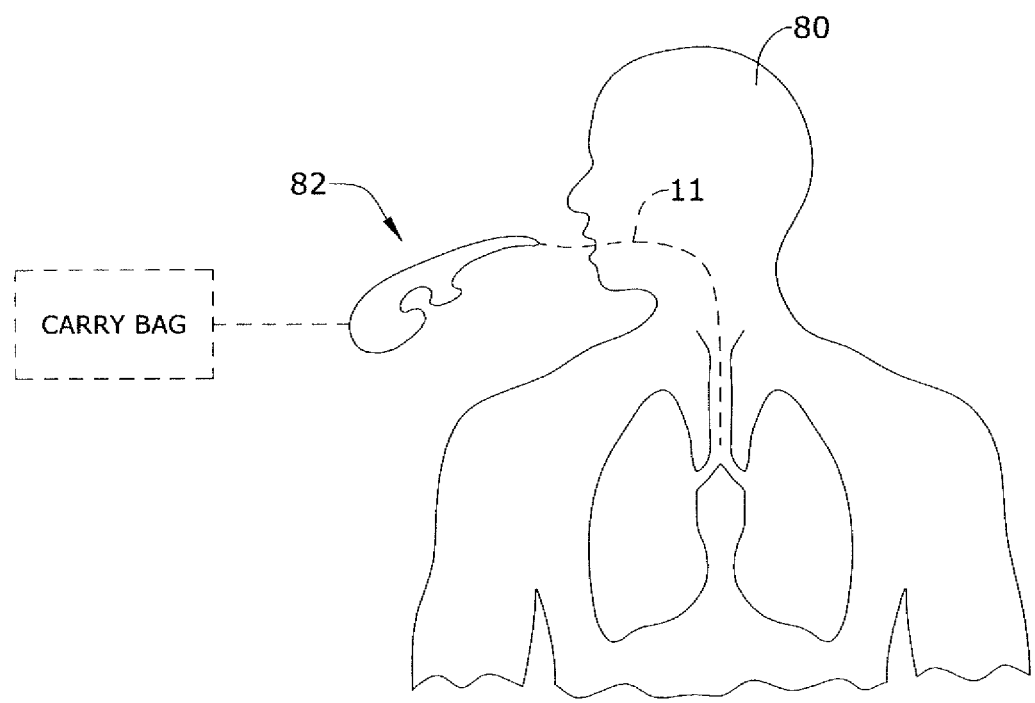
FIG. 7 shows a schematic view of one embodiment of the present invention shown in use.
Figure 8:
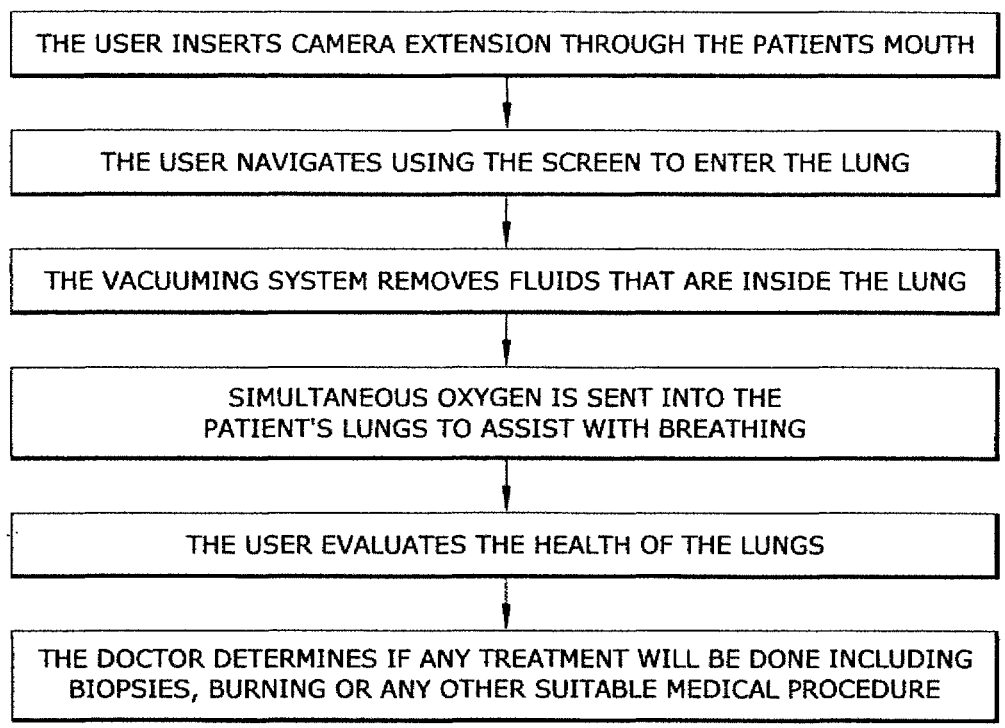
FIG. 8 shows a flow chart of one embodiment of the present invention.

As shown in FIG. 6, a carry-on bag for first responders 126 further comprises a housing attached to a handle 100. The housing further comprises cavities to store oxygen cylinders 102 and fluid samples 104. At least one adult sized lung endoscopy system 10 in a first cavity 105. At least one child sized lung endoscopy system 10 in a second cavity 106.

The housing further comprises at least on front camera screen 108, at least one secondary camera screen 110, a power switch and connection 112, a front camera switch 114, a secondary camera switch 116. The housing further comprises a vacuum switch 118 with line connection 122, at least one rechargeable battery 120. A plurality of swivel wheels 124 are attached to the housing. A carry bag 126 can be stored in the housing.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, ¶6. In particular, any use of "step of" in the claims is not intended to invoke the provision of 35 U.S.C. § 112, ¶6.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A lung endoscopy system, configured to provide portable data to a health care provider; the lung endoscopy system comprising:
    a handle housing, attached to a primary screen, a second screen, a third screen, and a fourth screen;
    an inflatable ball, joined to the housing and electrically coupled to a ball valve inflate switch, a ball valve deflate switch, and a pump;
    a power connection, electrically coupled to a power connector and an external power source on a wheel cart;
    a camera switch is electrically coupled to a left middle camera, a right middle camera, a 180-degree camera, and a front entry camera arranged on the handle housing;
    wherein the left middle camera, the right middle camera, the 180-degree camera, and the front entry camera are electrically coupled to at least one monitor on the wheel cart, and a second screen with a camera extension line.

2. The lung endoscopy system of claim 1, further comprising: a Wi-Fi television connection, communicatively coupled to the handle housing and configured to transmit to visual data to an external television screen.

3. The lung endoscopy system of claim 1, further comprising: a burn switch, arranged on the handle housing, joined to a knife with a burn line attached to the wheel cart.

4. The lung endoscopy system of claim 1, further comprising: a vacuum switch, arranged on the handle housing, and joined coupled to the wheel cart with a vacuum line at a vacuum source.

5. The lung endoscopy system of claim 1, further comprising: a freeze switch, arranged on the handle housing, and joined to the wheel cart with a freeze line.

6. The lung endoscopy system of claim 1, further comprising: A camera light switch, arranged on the handle housing and electrically coupled to a first LED on the left middle camera, a second LED on the right middle camera, a third LED on the 180-degree camera, and a fourth LED on the front entry camera.

\* \* \* \* \*